(12) United States Patent
Rausa et al.

(10) Patent No.: US 11,690,634 B2
(45) Date of Patent: Jul. 4, 2023

(54) NON-SHEDDING COUPLING METHOD AND SYSTEM FOR RELOADABLE HEMOSTASIS CLIP

(71) Applicant: BOSTON SCIENTIFIC SCIMED, INC., Maple Grove, MN (US)

(72) Inventors: Joseph Rausa, Littleton, MA (US); Collin Murray, Maynard, MA (US); Joseph W. King, Franklin, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 171 days.

(21) Appl. No.: 16/905,765

(22) Filed: Jun. 18, 2020

(65) Prior Publication Data
US 2021/0022744 A1 Jan. 28, 2021

Related U.S. Application Data

(60) Provisional application No. 62/877,879, filed on Jul. 24, 2019.

(51) Int. Cl.
*A61B 17/128* (2006.01)
*A61B 17/122* (2006.01)
*A61B 17/00* (2006.01)

(52) U.S. Cl.
CPC ........ *A61B 17/1285* (2013.01); *A61B 17/122* (2013.01); *A61B 2017/0034* (2013.01); *A61B 2017/00477* (2013.01); *A61B 2017/00818* (2013.01)

(58) Field of Classification Search
CPC . A61B 17/122; A61B 17/1222; A61B 17/128; A61B 17/1285; A61B 17/10; A61B 17/083; A61B 2017/0034; A61B 2017/00477; A61B 2017/00818
See application file for complete search history.

(56) References Cited

U.S. PATENT DOCUMENTS

2018/0153552 A1  6/2018  King et al.
2019/0159783 A1  5/2019  Lehtinen et al.

FOREIGN PATENT DOCUMENTS

| CN | 104546055 A | 4/2015 |
| EP | 1 829 489 | 9/2007 |
| JP | 2007507307 A | 3/2007 |
| JP | 2010525879 A | 7/2010 |
| JP | 2015532859 A | 11/2015 |

*Primary Examiner* — Brooke Labranche
(74) *Attorney, Agent, or Firm* — Fay Kaplun & Marcin, LLP

(57) ABSTRACT

A device for treating tissue includes a clip including clip arms and a coupler. Each of the clip arms extends from a proximal end to a distal end. Proximal ends of the clip arms are slidably received within a channel of a capsule. A proximal end of the capsule includes openings extending through a wall. The coupler is mounted over the proximal end of the capsule via deployment arms including engaging features extending laterally inward from an interior surface thereof to engage the openings of the capsule. The coupler includes retention arms configured to engage a corresponding portion of an applicator. When a pre-determined compressive force is applied to the coupler, the deployment arms are proximally slidable along the corresponding portion of the applicator to deflect the deployment arms out of engagement with the capsule so that the coupler is separable from the capsule.

17 Claims, 5 Drawing Sheets

NON-SHEDDING COUPLING METHOD AND SYSTEM FOR RELOADABLE HEMOSTASIS CLIP

PRIORITY CLAIM

The present disclosure claims priority to U.S. Provisional Patent Application Ser. No. 62/877,879 filed Jul. 24, 2019; the disclosure of which is incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be used.

SUMMARY

The present disclosure relates to a clipping system for treating tissue. The system includes clip including a pair of clip arms. Each of the clip arms extends from a proximal end to a distal end. Proximal ends of the clip arms are slidably received within a channel of a capsule to be moved between an open configuration and a closed configuration, a proximal end of the capsule including a pair of openings extending through a wall thereof. The system also relates a coupler mounted over the proximal end of the capsule and including a pair of deployment arms and a pair of retention arms, the deployment arms having engaging features received within the openings of the capsule. In addition, the system includes an applicator including an elongated flexible member and a control member extending therethrough. The control member includes a distal end configured to be connected to the clip arms to move the clip arms between the open configuration and the closed configuration, a distal end of the elongated flexible member including a projection extending about a periphery of the distal end thereof to engage corresponding retaining features of the retention arms. The deployment arms and the projection are configured so that, when a pre-determined compressive force is applied to the coupler during deployment of the clip, the deployment arms slide proximally along the projection such that the deployment arms deflect away from the bushing to disengage the engaging features therefrom so that the coupler is separable from the capsule.

In an embodiment, the retention features of the retention arms extend laterally inwardly from an interior surface of the retention arms toward a longitudinal axis of the coupler so that, to couple the bushing to the coupler, the bushing is inserted distally between the retention arms until the projection is moved distally past the retention features.

In an embodiment, the deployment arms include curved portions proximal of the engaging features, the curved portions curved inward toward a longitudinal axis of the coupler so that a diameter of the coupler between the curved portions is smaller than a diameter of the coupler along a remaining portion thereof.

In an embodiment, the each of the retention arms include a first protrusion extending laterally inward from an interior surface thereof, the first protrusion engaging a portion of the capsule to prevent a proximal movement of the capsule relative to the coupler.

In an embodiment, the each of the retention arms include a second protrusion extending laterally inward from an interior surface thereof, the second protrusion positioned distally of the retention features so that, when the bushing is coupled to the coupler, the projection is received between the second protrusion and the engaging features.

In an embodiment, a depth of the second protrusion is selected so that, when the pre-determined compressive force is applied to the coupler, the second protrusion is permitted to slide proximally past the protrusion to engage a proximal end of the protrusion.

In an embodiment, the coupler includes a distal portion extending about the proximal end of the capsule such that the pair of deployment arms and the pair of retention arms extend proximally therefrom.

In an embodiment, the retention arms diametrically oppose one another and the deployment arms diametrically oppose one another.

In an embodiment, the control member is connectable to the clip arms via a yoke configured to separate a proximal portion thereof, which is coupleable to the control member, from a distal portion thereof, which is connected to the proximal ends of the clip arms, when subject to a predetermined threshold force.

The present disclosure also relates to a clip device for treating tissue. The device includes a clip including a pair of clip arms, each of the clip arms extending from a proximal end to a distal end, proximal ends of the clip arms slidably received within a channel of a capsule to be moved between an open configuration and a closed configuration, a proximal end of the capsule including a pair of openings extending through a wall thereof. In addition, the device includes a coupler mounted over the proximal end of the capsule via a pair of deployment arms including engaging features extending laterally inward from an interior surface thereof to engage the pair of openings of the capsule, the coupler including retention arms configured to engage a corresponding portion of an applicator, the deployment arms configured so that, when a pre-determined compressive force is applied to the coupler, the deployment arms are proximally slidable along the corresponding portion of the applicator to deflect the deployment arms out of engagement with the capsule so that the coupler is separable from the capsule.

In an embodiment, the retention arms include retention features extending laterally inwardly from an interior surface of the retention arms toward a longitudinal axis of the coupler for engaging a corresponding portion of an applicator.

In an embodiment, the deployment arms include curved portions proximal of the engaging features, the curved portions curved inward toward a longitudinal axis of the coupler so that a diameter of the coupler between the curved portions is smaller than a diameter of the coupler along a remaining portion thereof.

In an embodiment, each of the retention arms include a first protrusion extending laterally inward from an interior surface thereof, the first protrusion engaging a portion of the capsule to prevent a proximal movement of the capsule relative to the coupler.

In an embodiment, each of the retention arms include a second protrusion extending laterally inward from an interior surface thereof, the second protrusion positioned distally of the retention features so that the corresponding portion of the applicator is receivable therebetween.

In an embodiment, a depth of the second protrusion is selected so that, when the pre-determined compressive force is applied to the coupler, the second protrusion is permitted to slide proximally past the corresponding portion of the applicator.

In addition, the present disclosure relates to a method for clipping a target tissue which includes coupling a capsule of a clip to a bushing of an applicator by inserting a distal portion of the bushing through a proximal end of a coupler mounted over a proximal end of a capsule of the clip so that a projection extending from a distal end of the bushing engages a pair of retention arms of the coupler, the coupler mounted over the proximal end of the capsule via engaging features of a pair of deployment arms received within corresponding openings extending through a wall of the capsule, the clip including a pair of clip arms, proximal ends of which are slidably received within a channel of the capsule; coupling a control member of the applicator to proximal ends of the clip arms; inserting the clip to a target area within a body via a working channel of an endoscope; and moving the clip between an open configuration, in which distal ends of clip arms are separated from one another, and closed configurations, in which the distal ends of the clip arms are drawn toward one another, until a target tissue is clipped between the clip arms, wherein the clip is moved between the open and closed configurations via a longitudinal movement of the control member relative to the clip.

In an embodiment, the retention arms include retention features extending laterally inwardly from an interior surface of the retention arms toward a longitudinal axis of the coupler so that the projection of the bushing engages the retention features when the bushing is inserted distally between the retention arms.

In an embodiment, the method further includes deploying the clip from the applicator by applying a pre-determined compressive force to the coupler to cause deployment arms of the coupler to slide proximally along the projection of the bushing so that the deployment arms deflect away from the bushing to disengage the engaging features from the openings of the capsule so that the coupler is separable from the capsule.

In an embodiment, each of the retention arms include a first protrusion extending laterally inward from an interior surface thereof, the first protrusion engaging a portion of the capsule to prevent a proximal movement of the capsule relative to the coupler when the pre-determined compressive force is applied to the coupler.

In an embodiment, each of the retention arms include a second protrusion extending laterally inward from an interior surface thereof so that the projection of the bushing is received between the second protrusion and the retention features, the second protrusion configured so that, when the pre-determined compressive force is applied to the coupler the second protrusion is forced proximally past the projection to engage a proximal end of the projection.

DETAILED DESCRIPTION

Figure 1:
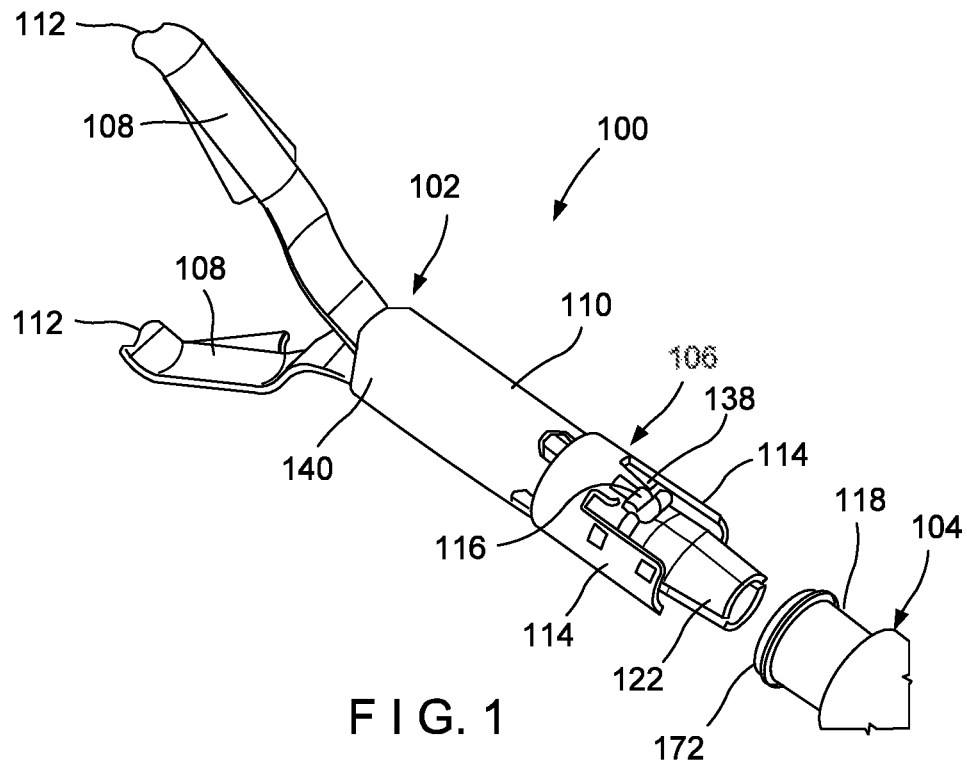
FIG. 1 shows a perspective view of a system according to an exemplary embodiment of the present disclosure.
Figure 2:
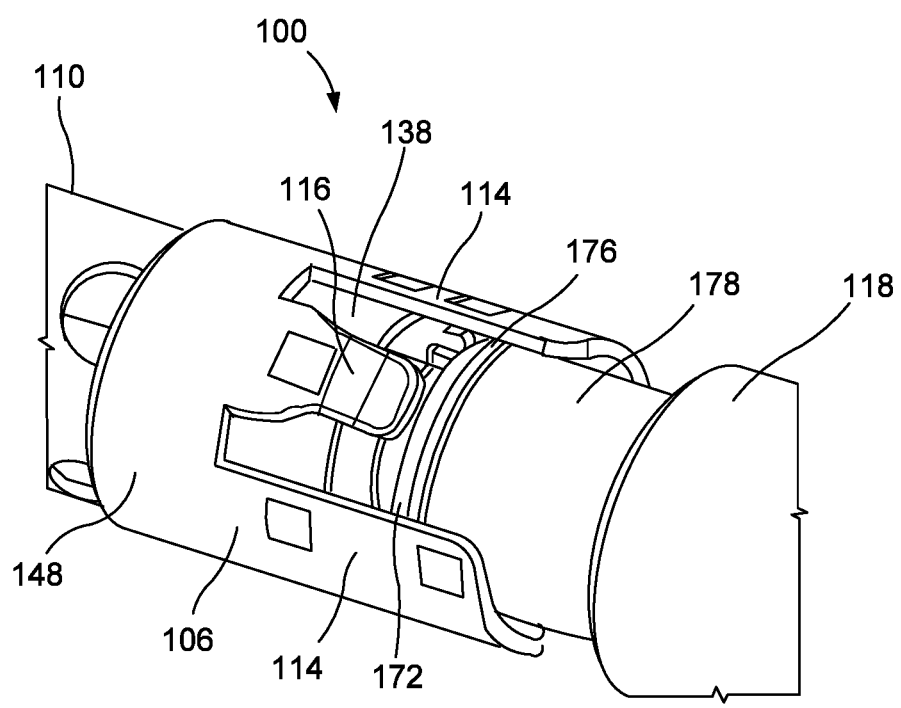
FIG. 2 shows an enlarged perspective view of a portion of the system of FIG. 1.
Figure 3:
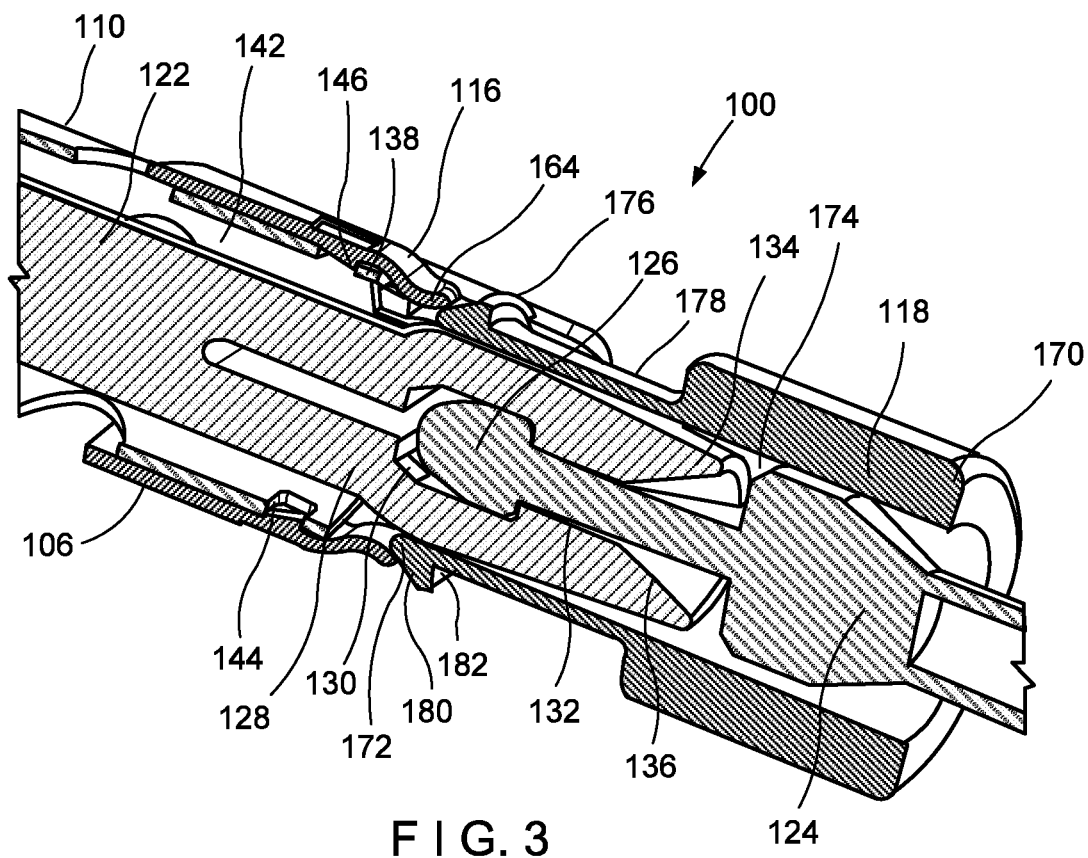
FIG. 3 shows a cross-sectional perspective view of a portion of the system of FIG. 1.
Figure 4:
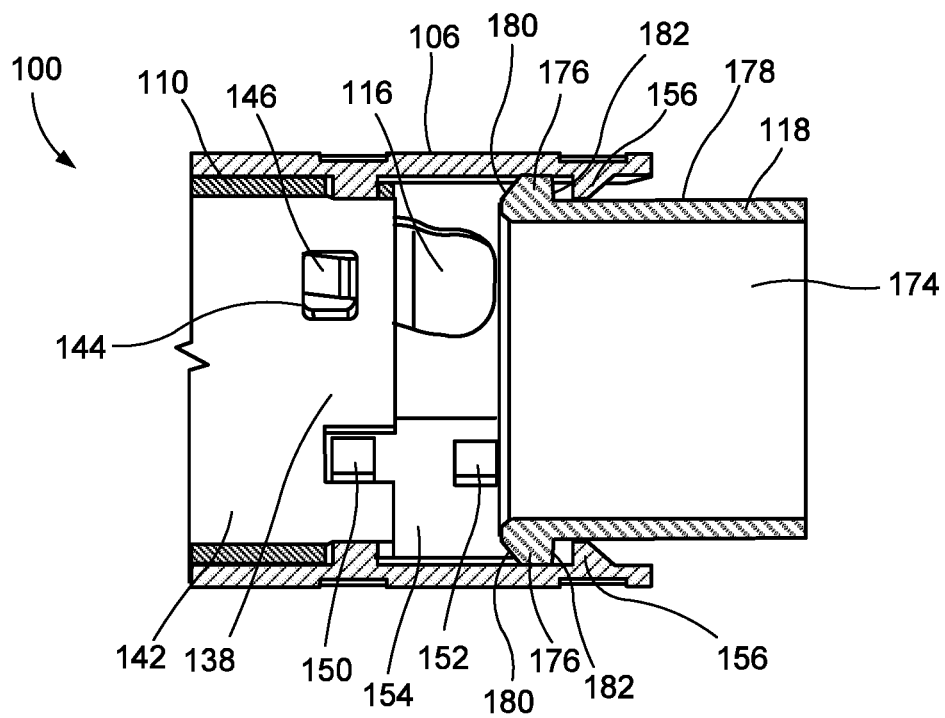
FIG. 4 shows a longitudinal cross-sectional view of a portion of the system of FIG. 1.

The present disclosure may be further understood with reference to the following description and the appended drawings, wherein like elements are referred to with the same reference numerals. The present disclosure relates to a clipping system and, in particular, relates to a reloadable endoscopic clipping system, in which a clip may be loaded onto a distal end of an applicator prior to an endoscopic procedure. Once a clip has been deployed at a desired target area in the body, the applicator may be reloaded with a new clip. Although shed parts (e.g., parts that are left in a body upon deployment of the clip) generally pass naturally from the body shed parts may become trapped in larger defects after closure.

Exemplary embodiments of the present disclosure comprise a clip including clip arms slidable within a capsule to move between an open configuration and a closed configuration to clip tissue, as desired. A proximal end of the capsule is loaded onto a bushing at a distal end of an applicator via a coupler which facilitates a releasable connection with the applicator while also minimizing or eliminating the potential for shed parts upon deployment of the clip. Prior to loading of the clip onto the applicator the coupler is coupled to the capsule. Upon deployment of the clip, however, the coupler is detached from the capsule to be removed from the body along with the applicator. It will be understood by those of skill in the art that the terms proximal and distal as used herein, are intended to refer to a direction toward and away from, respectively, a user of the device.

As shown in FIGS. 1-11, a reloadable clipping system 100 comprises a clip 102 configured to be loaded onto an applicator 104 via a coupler 106 prior to insertion of the system 100 into a body to clip target tissue therein. The clip 102 includes a pair of clip arms 108, proximal ends of which are slidably received within a capsule 110 so that the clip arms 108 may move between an open configuration, in which distal ends 112 of the clip arms 108 are separated from one another, and a closed configuration, in which distal ends 112 are drawn toward one another to grip tissue. The coupler 106 includes a pair of retention arms 114, which maintain a coupling between the clip 102 and, for example, a bushing 118 of the applicator 104 while the clip 102 is moved between the open and closed configurations during use. The coupler 106 also include a pair of deployment arms 116, which facilitate deployment of the clip 102 from the applicator 104. In particular, as will be described in further detail below, prior to loading of the clip 102 onto the applicator 104, the coupler 102 is coupled to the capsule 110 of the clip 102 to facilitate loading of the clip 102 onto the applicator 104 via the retention arms 114.

During deployment of the clip 102 over a target portion of tissue in the body, however, the clip 102 is moved proximally relative to the applicator 104 so that the deployments arms 116 are moved radially outward with respect to a longitudinal axis of the system 100, disengaging the coupler 106 from the capsule 110 so that the coupler 106 may be removed from the body along with the applicator 104. The coupler 106 stays attached to the bushing 118 even after detaching from the capsule 110. The coupler 106 will then have to be removed from the bushing 118 by a user prior to loading a new clip 102 onto the same applicator 104. Thus, deployment 102 of the clip 102 does not leave any shed parts in the body. The applicator 104 is configured so that, after deployment of the clip 102, a new clip 102 may be loaded onto the applicator 104 so that the same applicator 104 may be used to deliver the new clip 102 to a second portion of target tissue in the body. Each clip 102 according to this embodiment is stored in a cartridge 120, which facilitates loading of the clip assembly 102 onto the applicator 104.

As shown in FIGS. 1-4, the clip 102 includes the pair of clip arms 108, proximal ends of which are, in this embodiment, connected to one another via a yoke 122 slidably received within the capsule 110. In this embodiment, the clip arms 108 are biased toward the open configuration so that, when not constrained by the capsule 110, the clip arms 108 move under their natural bias to the open configuration in which the distal ends 112 of the clip arms 106 spread apart from one another to receive tissue therebetween. When the clip arms 108 are drawn into the capsule 110, the capsule 110 constrains the clip arms 108, holding the distal ends 112 together so that tissue may be gripped therebetween. The yoke 122 is longitudinally slidable within the capsule 110 to move the clip arms 108 proximally and distally relative to the capsule 110 between the open and closed configurations.

Each of the clip arms 108 extends from a proximal end connected to the yoke 122 to the distal end 112. The distal ends 112 of one or both of the clip arms 108 may include a tip extending laterally inward toward the other clip arm 108 with the tips including, for example, teeth, protrusions, spikes or other structures configured to grip tissue between the distal ends 112. One or both of the clip arms 108 may also include a locking feature configured to lock the clip arms 108 in the tissue gripping configuration after target tissue has been gripped as desired by the clip arms 108. In one embodiment, one or both of the clip arms 108 includes a locking tab extending laterally outward therefrom configured to engage a portion of the capsule 110 when the clip arms 108 have been drawn into the capsule 110 by a predetermined distance. For example, the locking tabs may be received within correspondingly sized, shaped and positioned locking windows extending laterally into or through a wall of the capsule 110 to lock the clip arms 108 relative to the capsule 110, in the tissue gripping configuration.

The yoke 122 is connected to the proximal ends of the clip arms 108 and is configured to be connected to an enlarged distal end 126 of a control member 124 of the applicator 104. In one embodiment, the yoke 122 of this embodiment includes a proximal portion 128 and a distal portion (not shown) configured to be separated from one another when subject to a force exceeding a predetermined threshold value. The proximal portion 128 and distal portion may, for example, be connected to one another via a welding, a decreased diameter portion, or an adhesive that breaks or otherwise separates when pre-determined force is exerted thereon. The distal portion may engage proximal portions of the clip arms 108 via, for example, a pair of protrusions extending through openings along proximal portions of the clip arms 108 so that the clip arms 108 are held in position relative to one another.

The proximal portion 128 is configured to engage the enlarged distal end 126 of the control member 124. In one embodiment, the proximal portion 128 includes a cavity 130 sized and shaped to receive the enlarged distal end 126 and a longitudinal slot 132 extending proximally from the cavity 130 to a proximal end 134 of the yoke 122. The longitudinal slot 132 is sized and shaped to receive a portion of the control member 124 extending proximally from the enlarged distal end 126.

In one embodiment, an opening of the longitudinal slot 132 at the proximal end 134 includes an angled surface 136 tapering toward a distal end thereof to facilitate insertion of the enlarged distal end 126 distally through the longitudinal slot 132 and into the cavity 130 during loading the clip 102 onto the applicator 104. The cavity 130 and the longitudinal slot 132 are configured so that, once the enlarged distal end 126 has been forced through the slot 132 into the cavity 130, the slot 132 retracts in diameter to prevent the enlarged distal end 126 from being proximally withdrawn therefrom. Thus, longitudinal movement of the control member 124 relative to the capsule 110 moves the clip arms 108 between the open and the closed configurations.

The capsule 110 extends longitudinally from a proximal end 138 to a distal end 140 and includes a channel 142 extending longitudinally therethrough. The channel 142 is sized and shaped to slidably receive the yoke 122 and the clip arms 108 therein. As described above, the capsule 110 of this embodiment also includes locking structures (e.g., locking recesses or windows) for engaging corresponding locking features (e.g., locking tabs) of the clip arms 108. The capsule 110, in this embodiment, also includes openings 144 extending through a wall thereof along the proximal end 138. The openings 144 are sized, shaped and configured to receive an engaging feature 146 of the deployment arms 116 of the coupler 106, as will be described in further detail below.

Figure 5:
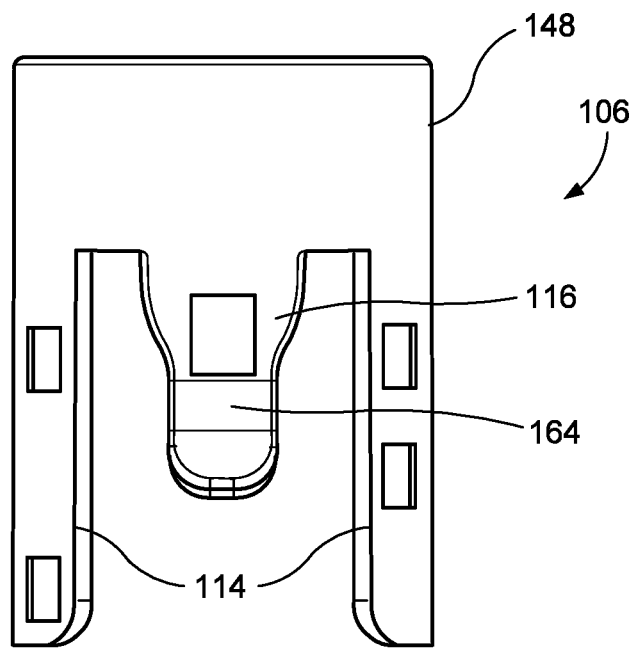
FIG. 5 shows a side view of a coupler according to the system of FIG. 1.
Figure 6:
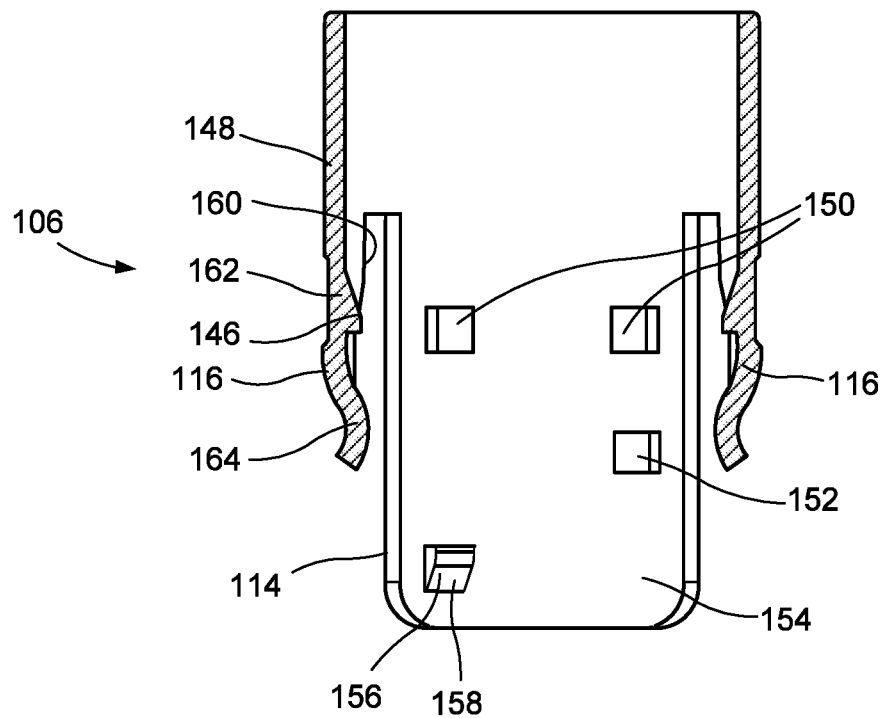
FIG. 6 shows a cross-sectional view of the coupler according the system of FIG. 1.

As described above, the coupler 106 is coupled to the proximal end 138 of the capsule 110 of the clip 102 prior to loading of the clip 102 onto the applicator 104. In this embodiment, the coupler 106 includes a distal portion 148 sized and shaped to be mounted over the capsule 110, the pair of retention arms 114 and the pair of deployment arms 116 extending proximally therefrom. The coupler 106, in this embodiment, may be formed of a stainles steel material and manufactured via, for example, metal stamping and rolling. As shown in FIGS. 5-6, in one embodiment, the distal portion 148 may be substantially ring shaped, with the retention arms 114 substantially diametrically opposing one another and the deployment arms 116 substantially diametrically opposing one another so that the retention arms and the deployment arms 116 alternate about a periphery of the coupler 106. In one embodiment, each of the retention arms 114 and the deployment arms 116 may be equally spaced from one another.

Each retention arm 114 includes a first protrusion 150 extending laterally (e.g., radially inward) from an interior surface 154 (i.e., a surface of the retention arms 114 which, in an operative configuration, faces toward the bushing 118) thereof along a distal portion thereof and a second protrusion 152 extending laterally (e.g., radially inward) from the interior surface 154 proximally of the first protrusion 150. The first protrusion 150 is sized, shaped and configured so that the coupler 106 may be slid distally over the proximal end 138 of the capsule 110 until the first protrusion 150 engages a portion of the capsule 110, preventing the coupler 106 from being moved any further distally relative thereto. Proximally of the second protrusion 152, the retention arm 114 includes a retention feature 156 configured as a protrusion extending laterally (e.g., radially inward) from the interior surface 154 to, as will be described in further detail below, engage a portion of the bushing 118 during a loading of the clip 102 onto the applicator 104. The retention feature 156 may be shaped to facilitate a distal insertion of a portion of the bushing 118 therepast (or a proximal movement of the coupler 106 over a portion of the bushing 118) during loading of the clip 102. In particular, the retention feature 156 may include an angled surface 158 tapering toward a proximal end thereof.

The second protrusion 152 is configured such that, when the retention feature 156 engages a corresponding portion of the bushing 118, a distal end 172 of the bushing 118 engages the second protrusion 152, preventing the bushing 118 from being moved any further distally relative to the coupler 106 during loading of the clip 102 onto the applicator 104 and during opening and closing of the clip 102. A depth of the second protrusion 152 (i.e., a distance by which the second protrusion extends from the interior surface 154) is, however, selected so that, when a pre-determined compressive force is applied to the coupler 106 during deployment of the clip 102 the second protrusion 152 is permitted to move proximally past the distal end 172 of the bushing 118 (i.e., the second protrusion 152 is sized and shaped to dictate deployment force), as will be described in further detail below. Additionally, the second protrusion 152 serves as a retention feature for the coupler 106 to stay engaged with the bushing 118 after the couple 106 separates from the capsule 110. It will be understood by those of skill in the art, that in some embodiments, the retention arms 114 may include more than one of each of the first protrusion 150, second protrusion 152 and the retention feature 156.

Each deployment arm 116 includes the engaging feature 146 along a distal portion thereof. The engaging feature 146 extends laterally inward from an interior surface 160 of the deployment arm 116 (i.e., a surface of the deployment arm 116 facing toward the bushing 118, in the operative configuration). The engaging feature 146 is configured so that, when the coupler 106 is assembled with the clip 102 prior to loading of the clip 102, the coupler 106 may be moved distally over the proximal end 138 of the capsule 110 until the engaging feature 146 is snapped into a corresponding one of the openings 144 of the capsule 110 and the first protrusion 150 engages the capsule 110 preventing further distal movement of the coupler 106 relative to the capsule 110.

In this embodiment, the engaging feature 146 includes an angled surface 162, which tapers toward a distal end thereof, to facilitate distal movement of the coupler 106 over the capsule 110 during the assembly of the coupler 106 with the capsule 110. It will be understood by those of skill in the art that, once the coupler 106 is assembled with the clip 102, the angled surface 162 of the engaging feature 146 prevents a proximal movement of the coupler 106 relative to the capsule 110, while the first projections 150 prevents a distal movement of the coupler 106 relative to the capsule 110.

Each deployment arm 116 also includes a curved portion 164 proximal of the engaging feature 146. The curved portion 164 is curved inward toward a longitudinal axis of the coupler 106 so that a distance between the curved portions 164 of the pair of deployment arms 116 is smaller than a distance between remaining portions of the deployment arms 116. For example, a diameter between the curved portions 164 is smaller than a diameter of a remaining portion of the coupler 106. Thus, as will be described in further detail below, when the curved portions 164 are moved proximally over a portion of the bushing 118, the deployment arms 116 deflect radially outward so that the engaging features 146 are disengaged from the openings 144 of the capsule 110.

Although the deployment arms 116 are shown and described as including curved portions 164, it will be understood by those of skill in the art that the deployment arms 116 may include other structure or features for engaging the bushing 118 to cause an outward deflection or deformation of the deployment arms 116. It will also be understood by those of skill in the art that a force required to deflect or deform the deployment arms 116 may be controlled by adjusting a length and/or width of the deployment arms 116 or a distance between the curved portions 164. It will also be understood by those of skill in the art that a depth of the engaging features 146 (i.e., a distance by which the engaging feature 146 extends from the interior surface 160) may also be adjusted to increase or decrease a retention of the coupler 106 onto the capsule 110.

Figure 7:
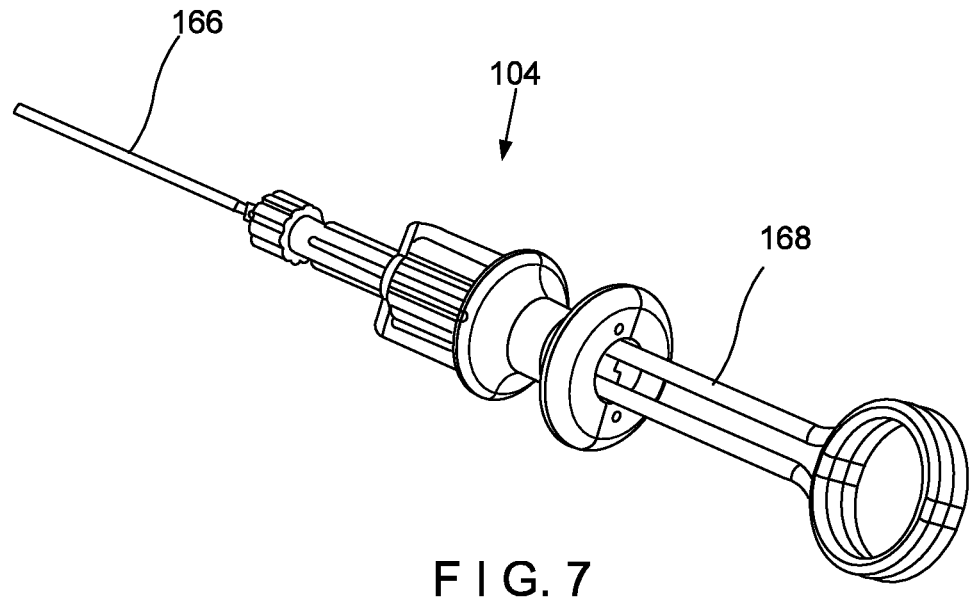
FIG. 7 shows a perspective view of an applicator according to the system of FIG. 1.

As shown in FIG. 7, the applicator 104 includes a flexible member 166 such as, for example, a catheter extending from a proximal end connected to a handle portion 168 that remains outside of the body during the clipping of target tissue, to a distal end including, for example, the bushing 118 for connecting the applicator 104 to the clip 102. The control member 124 extends through the flexible member 166 from a proximal end connected to the handle portion 168, which includes actuators for controlling a movement of the clip 102 once the clip 102 has been loaded onto the applicator 104, to the enlarged distal end 126.

In an embodiment, the bushing 118 is connected to the distal end of the flexible member 166 and is configured to be connected to the clip 102 via the coupler 106, which is preassembled with the clip 102. The bushing 118 extends from a proximal end 170 to a distal end 172 and includes a channel 174 extending therethrough so that, when the bushing 118 is coupled to the clip 102 via the coupler 106, the channel 174 of the bushing 118 is substantially aligned with the channel 142 of the capsule 110. In an embodiment, the distal end 172 of the bushing 118 includes a projection 176 extending about a periphery of the bushing 118, the projection 176 extending radially outward from an exterior surface 178 along the distal end 172. A distal end 180 of the projection 176 is tapered to facilitate insertion of the projection 176 distally past the retention feature 156. The proximal end 182 of the projection 176 is configured to engage the retention feature 156. As described above, when the clip 102 is loaded onto the applicator 104 by moving the projection 176 distally past the retention feature 156, the projection 176 is received between the second projection 152 and the retention feature 156, holding the projection 176 therebetween during use of the clip 102—e.g., opening and closing of the clip arms 108.

Figure 8:
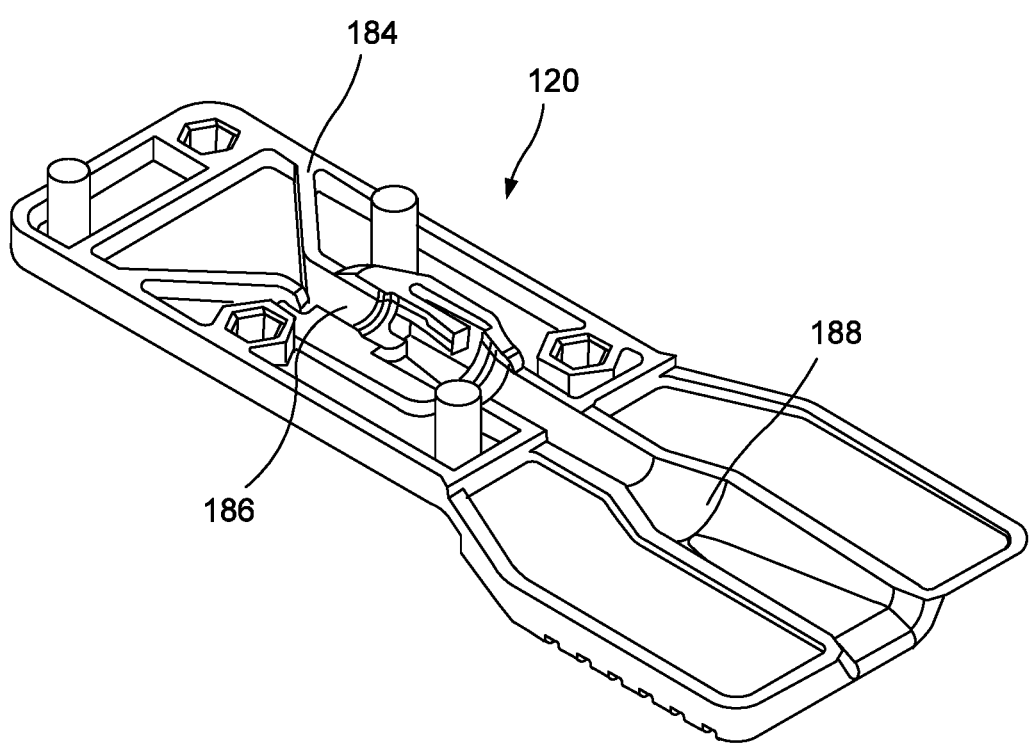
FIG. 8 shows a perspective view of a cartridge according to the system of FIG. 1.

Prior to being loaded on the applicator 104, the clip 102 of this embodiment is stored in the cartridge 120, which is configured to facilitate loading of the clip assembly 102 on the applicator 104. The cartridge 120, as shown in FIG. 8, is configured as a storage container including a base 184 and lid (not shown), within which a space 186 sized and shaped to house the clip 102 is defined. It should be noted that although FIG. 8 shows only the base 184 of the cartridge 120, a corresponding lid is coupled to the base 184 to completely enclose the clip 102. In this embodiment, the clip 102 is stored within the cartridge 120 in the open configuration, with the coupler 106 preassembled with the capsule 110. Extending proximally from the space 186 is a longitudinal slot 188 through which the distal portion of the applicator 104 is inserted to be coupled to the clip assembly 102, as will be described in further detail below.

Figure 9:
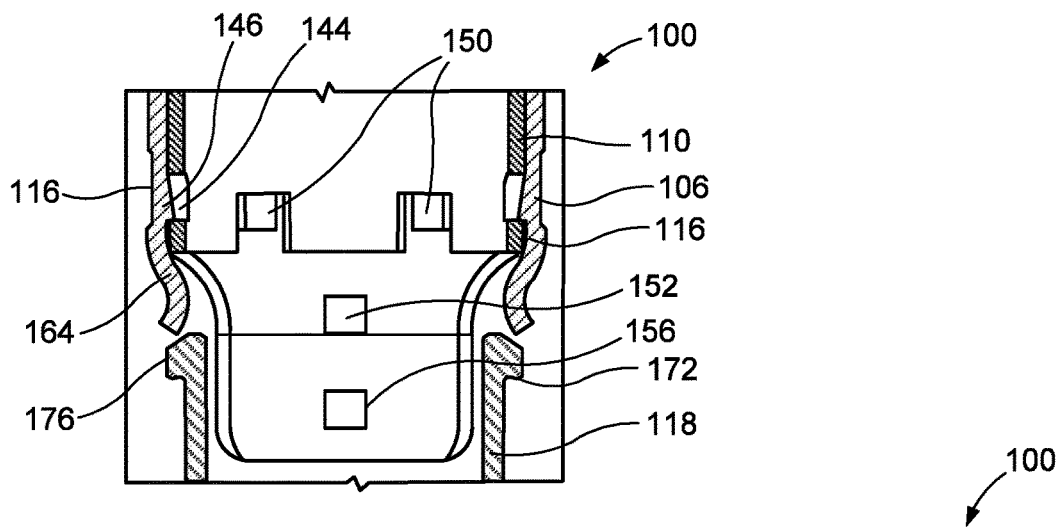
FIG. 9 shows a partially transparent side view of the coupler and a bushing of the system of FIG. 1, upon loading of a clip onto the applicator.

During loading of the clip 102 onto the applicator 104, a distal portion of the applicator 104, including the bushing 118, is inserted through the longitudinal slot 188 of the cartridge 120, which houses the assembled clip 102 and coupler 106. As described above, the coupler 106 is mounted over the proximal end 138 of the capsule 110 such that the engaging features 146 of the deployment arms 116 are received within the corresponding openings 144 of the capsule 110 and the first projections 150 engage a portion of the capsule 110. In one embodiment, the distal end 172 of the bushing 118 may be moved distally between the retention arms 114 of the coupler 106 so that the projection 176 is moved distally therepast and is received between the second projection 152 and the retention feature 156, as shown in FIG. 9. Once the bushing 118 is coupled to the clip 102 via the coupler 106, the control member 124 is moved distally relative to the bushing 118 to be coupled to the clip arms 108 via the yoke 122. In particular, the enlarged distal end 126 of the control member 124 may be inserted into the cavity 130 of the yoke 122 via the slot 132.

In another embodiment, the control member 124 may be coupled to the yoke 122 prior to coupling the bushing 118 to the coupler 106 so that upon coupling the control member 124 to the yoke 122, the capsule 110 may be moved proximally relative to the bushing 118 via a proximal motion of the control member 124 so that the coupler 106 is moved proximally over the distal end 172 of the bushing 118 to engage the projection 176. Once both the control member 124 and the bushing 118 have been coupled to the clip 102, loading of the clip 102 onto the applicator 104 is complete, and the clip 102 may be drawn proximally out of the cartridge via the longitudinal slot 188.

In use, after the clip 102 has been loaded onto the applicator 104, the clip 102, in the closed configuration, is inserted into the body to a location adjacent to target tissue via, for example, a working channel of an endoscope. Once the clip 102 has reached the target tissue, the clip 102 is moved toward the open configuration to receive the target tissue between the distal ends 112 of the clip arms 108. The clip 102 may be moved between the open and the closed configurations until the target tissue has been clipped between the clip arms 108, as desired. Once the clip 102 is in the closed configuration clipping the target tissue as desired, the control member 124 (e.g., via actuators of the handle portion 168) is moved proximally with respect to the capsule 110 until locking features of the clip arms 108 engage corresponding locking structures of the capsule 110, locking the clip arms 108 relative to the capsule 110 in the closed configuration.

Figure 10:
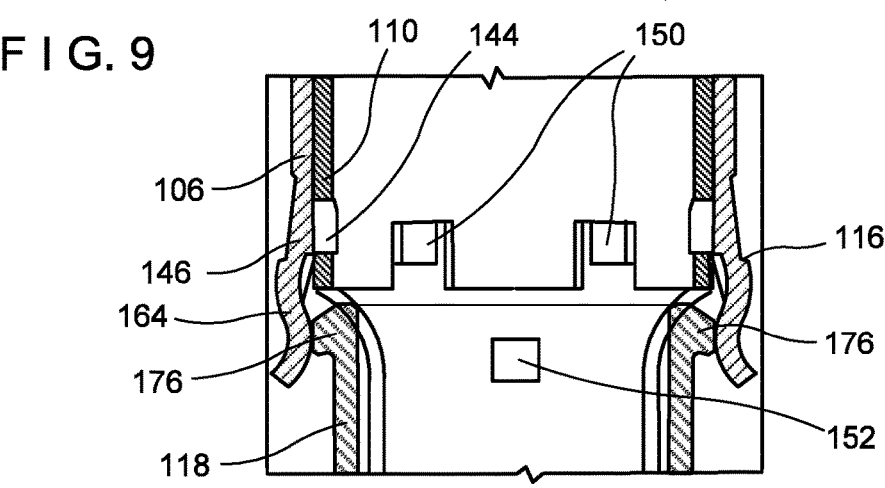
FIG. 10 shows a partially transparent side view of the coupler and the bushing of the system of FIG. 1, during a deployment of the clip.

To free the clip 102 from the applicator 104, the control member 124 is drawn further proximally until the coupler 106 is drawn proximally against the bushing 118 and a compressive load on the coupler 106 exceeds a predetermined threshold value, forcing the second protrusion 152 proximally past the projection 176 of the bushing 118 while also causing the curved portions 164 of the deployment arms 116 to slide proximally over projection 176, as shown in FIG. 10. As the curved portions 164 move proximally over the projection 176, the deployment arms 116 are deflected radially outward so that the engaging features 146 of the deployment arms 116 are moved out of engagement with the openings 144 of the capsule 110 and the second protrusion 152 is moved proximally past the proximal end 182 of the projection 176.

Figure 11:
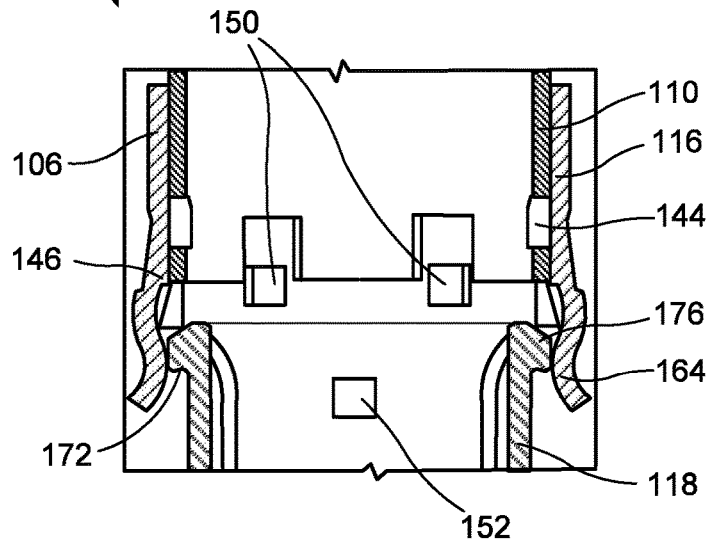
FIG. 11 shows a partially transparent side view of the coupler and the bushing system of FIG. 1, upon deployment of the clip.

As shown in FIG. 11, the second protrusion 152 engages the proximal end 182 of the projection so that the coupler 106 remains engaged to the bushing 118 while being disengaged from the capsule 110. The user continues to exert proximal force on the control member 124 until the yoke 122 breaks, fails or otherwise separates, releasing the clip 102, from the control member 124. Thus, the applicator 104, with the coupler 106 coupled thereto, may be removed from the body 102, leaving just the clip 102 in place clipping the target tissue. The entire applicator 104, including the control member 124, the coupler 106 and the proximal portion 128 of the yoke 122 may then be withdrawn proximally from the body leaving the clip 102 clipped over the target tissue. If so desired, a new clip 102 may be loaded onto the applicator 104, in the same manner as described above, so that the system 100 may then be used to clip a second portion of tissue. This process may be repeated using the same applicator 104 as many times as needed or desired.

It will be apparent to those skilled in the art that various modifications may be made in the present disclosure, without departing from the scope of the disclosure.

What is claimed is:

1. A clipping system for treating tissue, comprising:
a clip including a pair of clip arms, each of the clip arms extending from a proximal end to a distal end, proximal ends of the clip aims slidably received within a channel of a capsule to be moved between an open configuration and a closed configuration, a proximal end of the capsule including a pair of openings extending through a wall thereof;
a coupler mounted over the proximal end of the capsule and including a pair of deployment arms having engaging features received within the openings of the capsule, the coupler further including a pair of retention arms; and
an applicator including an elongated flexible member and a control member extending therethrough, the control member including a distal end configured to be connected to the clip arms to move the clip arms between the open configuration and the closed configuration, a distal end of the elongated flexible member including a bushing having a projection extending about a periphery of the distal end thereof to engage corresponding retention features of the retention arms to couple the bushing to the coupler, the deployment arms and the projection configured so that, when a pre-determined compressive force is applied to the coupler during deployment of the clip, the deployment arms slide proximally along the projection such that the bushing deflects the deployment arms radially outward to disengage the engaging features from the capsule so that the coupler is separable from the capsule while remaining coupled to the bushing.

2. The system of claim 1, wherein the retention features of the retention arms extend laterally inwardly from an interior surface of the retention arms toward a longitudinal axis of the coupler so that, to couple the bushing to the coupler, the bushing is inserted distally between the retention arms until the projection is moved distally past the retention features.

3. The system of claim 1, wherein the deployment arms include curved portions proximal of the engaging features, the curved portions curved inward toward a longitudinal axis of the coupler so that a diameter of the coupler between the curved portions is smaller than a diameter of the coupler along a remaining portion thereof.

4. The system of claim 1, wherein each of the retention arms includes a first protrusion extending laterally inward from an interior surface thereof, the first protrusion of each of the retention arms engaging a corresponding portion of the capsule to prevent a proximal movement of the capsule relative to the coupler.

5. The system of claim 4, wherein each of the retention arms includes a second protrusion extending laterally inward from the interior surface thereof, the second protrusion of each of the retention arms being positioned distally of the retention feature of the corresponding retention arm so that, when the bushing is coupled to the coupler, the projection is received between the second protrusion and the engaging features.

6. The system of claim 5, wherein a depth of the second protrusion is selected so that, when the pre-determined compressive force is applied to the coupler, the second protrusion is permitted to slide proximally past the projection to engage a proximal end of the second protrusion.

7. The system of claim 1, wherein the coupler includes a distal portion extending about the proximal end of the capsule such that the pair of deployment arms and the pair of retention arms extend proximally therefrom.

8. The system of claim 7, wherein the retention arms diametrically oppose one another and the deployment arms diametrically oppose one another.

9. The system of claim 1, wherein the control member is connectable to the clip arms via a yoke configured to separate a proximal portion thereof, which is coupleable to the control member, from a distal portion thereof, which is connected to the proximal ends of the clip aims, when subject to a predetermined threshold force.

10. The system of claim 1, wherein the coupler is configured to be coupled to the capsule prior to loading of the clip onto the applicator.

11. The system of claim 1, wherein the coupler is configured to disengage from the capsule during deployment while remaining attached to the bushing so that the coupler may be removed from a living body along with the applicator.

12. A clip device for treating tissue, comprising:
a clip including a pair of clip arms, each of the clip arms extending from a proximal end to a distal end, proximal ends of the clip arms slidably received within a channel of a capsule to be moved between an open configuration and a closed configuration, a proximal end of the capsule including a pair of openings extending through a wall thereof; and
a coupler mounted over the proximal end of the capsule via a pair of deployment arms, including engaging features extending laterally inward from an interior surface thereof to engage the pair of openings of the capsule, the coupler including retention arms configured to engage a bushing of an applicator to couple the bushing to the coupler, the deployment arms configured so that, when a pre-determined compressive force is applied to the coupler, the deployment arms are proximally slidable along the corresponding portion of the applicator so that the bushing deflects the deployment arms out of engagement with the capsule and the coupler is separable from the capsule while remaining coupled to the bushing.

13. The device of claim 12, wherein the retention arms include retention features extending laterally inwardly from an interior surface of the retention arms toward a longitudinal axis of the coupler for engaging a corresponding portion of an applicator.

14. The device of claim 13, wherein each of the retention an is includes a second protrusion extending laterally inward from an interior surface thereof, each of the second protrusions being positioned distally of the retention feature of the corresponding retention arm so that the corresponding portion of the applicator is receivable therebetween.

15. The device of claim 14, wherein a depth of the second protrusion is selected so that, when the pre-determined compressive force is applied to the coupler, the second protrusion is permitted to slide proximally past the corresponding portion of the applicator.

16. The device of claim 12, wherein the deployment arms include curved portions proximal of the engaging features, the curved portions curved inward toward a longitudinal axis of the coupler so that a diameter of the coupler between the curved portions is smaller than a diameter of the coupler along a remaining portion thereof.

17. The device of claim 12, wherein each of the retention aims includes a first protrusion extending laterally inward from an interior surface of the corresponding retention arm, the first protrusion engaging a portion of the capsule to prevent a proximal movement of the capsule relative to the coupler.

* * * * *